(12) United States Patent
Olah et al.

(10) Patent No.: US 8,816,137 B2
(45) Date of Patent: Aug. 26, 2014

(54) EFFICIENT AND ENVIRONMENTALLY FRIENDLY PROCESSING OF HEAVY OILS TO METHANOL AND DERIVED PRODUCTS

(75) Inventors: George A. Olah, Beverly Hills, CA (US); G.K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 358 days.

(21) Appl. No.: 12/755,997

(22) Filed: Apr. 7, 2010

(65) Prior Publication Data
US 2010/0274060 A1    Oct. 28, 2010

Related U.S. Application Data

(60) Provisional application No. 61/173,513, filed on Apr. 28, 2009.

(51) Int. Cl.
| C07C 29/88 | (2006.01) |
| C07C 29/90 | (2006.01) |
| C07C 31/04 | (2006.01) |

(52) U.S. Cl.
USPC .................... 568/840; 568/913; 568/914

(58) Field of Classification Search
USPC .......................... 568/885, 884, 903
See application file for complete search history.

(56) References Cited

U.S. PATENT DOCUMENTS

| 3,265,614 A * | 8/1966 | Matthew ............. 208/222 |
| 3,862,899 A | 1/1975 | Murphy et al. ............. 208/93 |
| 3,993,457 A * | 11/1976 | Cahn et al. .............. 48/197 R |
| 4,093,029 A | 6/1978 | Weisz et al. ................ 166/305 |
| 4,395,495 A | 7/1983 | Cummings ................. 518/704 |
| 4,589,973 A | 5/1986 | Minden .................. 208/410 |
| 4,640,766 A | 2/1987 | Post et al. ................ 208/111 |
| 5,599,638 A | 2/1997 | Surampudi et al. ........... 429/333 |
| 6,187,465 B1 * | 2/2001 | Galloway .................... 429/410 |
| 7,132,183 B2 * | 11/2006 | Galloway .................... 429/426 |
| 2005/0025701 A1 * | 2/2005 | Bhat et al. .................. 423/652 |
| 2007/0254969 A1 * | 11/2007 | Olah et al. ................... 518/726 |
| 2008/0319093 A1 | 12/2008 | Olah et al. ................... 518/700 |
| 2010/0166647 A1 | 7/2010 | Osawa et al. ................ 423/651 |

FOREIGN PATENT DOCUMENTS

| EP | 0 159 759 B1 | 10/1985 |
| EP | 1 835 165 A1 | 9/2007 |
| EP | 1 839 743 A1 | 10/2007 |
| EP | 2 075 227 A1 | 7/2009 |
| GB | 1 545329 A | 5/1979 |
| WO | WO 2006/113294 A1 | 10/2006 |
| WO | WO 2007/014487 A1 * | 2/2007 |
| WO | WO 2008/047676 A1 | 4/2008 |
| WO | WO 2008/157673 A1 | 12/2008 |

OTHER PUBLICATIONS

International Search Report and Written Opinion of the International Searching Authority, Application No. PCT/US2010/030254, Oct. 6, 2010.
Ward, "Hydrocracking processes and catalysts," Fuel Processing Technology, 35:55-85 (1993).

* cited by examiner

Primary Examiner — Rosalynd Keys
(74) Attorney, Agent, or Firm — Winston & Strawn LLP

(57) ABSTRACT

The invention provides for a method for processing heavy oil from any sources including tar sands, oil shales, varied residues in a bi-reforming process utilizing reaction conditions with steam and carbon dioxide sufficient to form a mixture of hydrogen and carbon monoxide to form methanol. Methanol produced can be dehydrated to form dimethyl ether, with water produced being recycled back to the bi-reforming process.

11 Claims, No Drawings

US 8,816,137 B2

EFFICIENT AND ENVIRONMENTALLY FRIENDLY PROCESSING OF HEAVY OILS TO METHANOL AND DERIVED PRODUCTS

CROSS-REFERENCE TO RELATED APPLICATIONS

This application claims the benefit of U.S. application No. 61/173,513 filed Apr. 28, 2009, the entire content of which is incorporated herein by reference thereto.

BACKGROUND

Although fossil fuels still have a wide application and high demand, they have limitations due to their finite reserve, their combustion produce carbon dioxide and thus contribute to global warming.

More abundant heavy oils increasingly are becoming a source of fuels and raw materials in various fields, such as the transportation sector, chemical, petrochemical, plastics, and rubber industries. The utilization and upgrading of heavy oils to higher value products is of great significance. Extensive heavy oil sources include much of the reserves in Venezuela, tar sands in Western Canada, shale oils in the Rocky Mountains, etc. Economic recovery and utilization of these reserves represent however, significant challenges.

The present invention discloses a new way to utilize heavy oil sources to produce methanol and derived products to be used in the context of the "methanol economy". Fossil fuel sources such as petroleum oil, natural gas and coal can be converted by known processes, including our previously disclosed patent applications into methanol and dimethyl ether by chemical recycling of carbon dioxide. Methanol and dimethyl ether are used as transportation fuels, as substitutes for gasoline and diesel fuel in ICE-powered vehicles with some needed modifications to the existing engines and fuel systems, as well as in fuel cells. By contrast with hydrogen, methanol storage and use does not require any new infrastructure including expensive pressurization and liquefaction. Because it is a liquid at room temperature, it can be easily handled, stored, distributed and used in vehicles. It is also an ideal hydrogen carrier for fuel cells and can be used in direct oxidation methanol fuel cells (DMFC). Dimethyl ether although a gas at room temperature, can be easily stored under modest pressure and used effectively as substitute for diesel fuels, liquefied natural gas (LNG) liquefied petroleum gas (LPG) and household gas.

In addition to use as fuels, methanol, dimethyl ether and their derived products have significant applications and uses. They are starting materials for varied chemical products including their catalytic conversion to olefins such as ethylene and propylene with smaller amounts of butenes, higher olefins, alkanes, and aromatics. They are thus convenient starting materials for synthetic hydrocarbons and their products.

Methanol can also be used as a source of single cell proteins. A single cell protein (SCP) refers to a protein produced by a microorganism, which degrades hydrocarbon substrates while gaining energy. The protein content depends on the type of microorganism, e.g., bacteria, yeast, mold, etc. SCP's have many uses, including as food and animal feed.

Considering the wide uses of methanol and dimethyl ether, it is clearly desirable to have improved and efficient methods for their production. The usual processing of heavy oils derived from unconventional sources such as tar sands, shale oils, etc. is costly, highly energy consuming and usually possible only in specific refineries. Thus, improvements in the processing, transportation and storage of heavy oils are desired and these are now provided by the present invention.

SUMMARY OF THE INVENTION

The present invention discloses new efficient and environmentally friendly processing of heavy petroleum oils obtained from any unconventional oil source such as tar sands, oil shales, petroleum oil residues (containing heavy asphaltenes and maltenes) into methanol and dimethyl ether, following their recovery breakdown and purification by any process practiced for such to obtain a heavy crude oil. It is then processed instead of usual refining via a bi-reforming process using carbon dioxide to produce an approximately 2:1 mol ratios of CO and $H_2$ which then can be converted to methanol, dimethyl ether or their derived products to be used as fuels, energy storage and starting materials for varied synthetic hydrocarbon and products produced therefrom. The heavy oil recovery can also include in situ gasification or heat treatment with any available heat source including natural gas or any available alternative energy, as well as atomic energy to enhance API index and to remove impurities such as sulfur and metals.

DETAILED DESCRIPTION OF THE PREFERRED EMBODIMENTS

The invention relates to the recovery of heavy oil from any source after their separation and purification involving but not limiting, tar sands, oil shales, various heavy oil deposits or residues thereof, and converting them to methanol and/or dimethyl ether by-passing the usual refining of the heavy oils. Methanol and dimethyl ether thus produced find utility in numerous applications, either alone, as fuels, storage and transportation materials or upon subsequent conversion to synthetic hydrocarbons and their varied products.

In one embodiment of the invention, heavy crude oils are separated and purified from harmful contaminants by known methods and are converted by reaction with carbon dioxide. The separation and purification includes breaking down extremely heavy asphaltene and maltene components contained in the heavy oil. Any of the known processes for such can be used including, without limitation, varied thermal or catalytic processes, including coking combined with vacuum treatment, which provides besides gaseous hydrocarbons, naptha and coal like residues and about 60% lighter oil with a good API index of 30-40. Impurities, mainly sulfur and metals, are also removed in the involved cracking-hydrogenation processes. More than 99.8% of these impurities are removed. The treated and purified derived crude oils can then directly processed using a suitable combination of steam ($H_2O$) and dry ($CO_2$) reforming to produce approximately a 1:2 mixture of carbon monoxide (CO) and hydrogen ($H_2$). A bi-reforming process utilizing methane and carbon dioxide is disclosed in US 2008/0319093 and in WO 2008/157673. This process utilizes a specific combination of steam ($H_2O$) and dry ($CO_2$) reforming, practiced in two steps or combined in a single step. The method comprises reacting methane gas under a combination of conditions of steam (wet) and dry ($CO_2$) reforming in a specific molar ratio of reactants sufficient to form a mixture of hydrogen/carbon dioxide ($H_2$/CO) in a molar ratio of about 2:1, preferably between 2:1 and 2.1:1, and most preferably about 2.05:1; the ratios that are sufficient to convert such mixture of $H_2$ and CO exclusively to methanol or dimethyl ether. Advantageously, the reactants or mixture of reactants is treated without separation of its components to convert substantially all the reactants to methyl alcohol or, if desired, to dimethyl ether without the production of significant by-products. Remaining residues are used for their needed heat values via their combustion. The present invention now discloses the use of a bi-reforming process for treating heavy oils derived from various sources with carbon dioxide, thus bypassing their costly and energy consuming reforming to directly produce methanol and/or dimethyl ether and their derived products.

The individual steps of the bi-reforming process of the invention for the formation of methanol and dimethyl ether are illustrated by the following reactions:

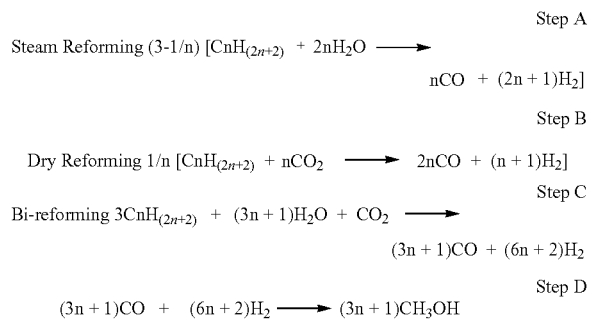

Step A
Steam Reforming $(3-1/n)\ [CnH_{(2n+2)}\ +\ 2nH_2O \longrightarrow nCO\ +\ (2n+1)H_2]$ Step B
Dry Reforming $1/n\ [CnH_{(2n+2)}\ +\ nCO_2 \longrightarrow 2nCO\ +\ (n+1)H_2]$ Step C
Bi-reforming $3CnH_{(2n+2)}\ +\ (3n+1)H_2O\ +\ CO_2 \longrightarrow (3n+1)CO\ +\ (6n+2)H_2$ Step D
$(3n+1)CO\ +\ (6n+2)H_2 \longrightarrow (3n+1)CH_3OH$ The bi-reforming process of producing methanol from heavy oil can be conducted by carrying out steps A and B separately. The products of reforming of steps A and B are mixed together before being introduced into the methanol producing step D. The steam reforming step is carried out by reacting heavy oil and steam in an appropriate molar ratio over a catalyst between by well-known procedures. The dry reforming step is carried by reacting heavy oil and carbon dioxide also in an appropriate molar ratio over a catalyst between 800° C. and 850° C.

The bi-reforming process of producing methanol can also be practiced by combining the two reforming steps A and B into a single reforming step C by reacting the heavy oil, steam and carbon dioxide in the mentioned molar ratio over a catalyst between 800° C. and 1100° C.

In a specific embodiment of the invention, a specific combination of steam and dry reforming of heavy oil is used to achieve a molar ratio of $H_2$ and CO of at least 2 moles hydrogen to 1 mole of carbon monoxide for the subsequent conversion to methanol. In another specific embodiment of the bi-reforming process, heavy oil is treated with steam and carbon dioxide in the specified molar ratio in a temperature range from about 800° C. to about 1100° C., preferably from about 800° C. to about 850° C. To allow conversion, a catalyst or combination of catalysts can be used. These catalysts include any suitable metal or metal oxide, including without limitation a metal such as V, Ti, Ga, Mg, Cu, Ni, Mo, Bi, Fe, Mn, Co, Nb, Zr, La or Sn, and corresponding oxides of such metals. These catalysts may be used as a single metal, or a combination of a metal and metal oxide, or a combination of metal oxides, supported on a suitable support such as a high surface area nanostructured oxide support such as fumed silica or fumed alumina. By way of example, NiO, metal-metal oxides such as $Ni-V_2O_5$, $(M_2O_3-V_2O_5)$, and $NiO:V_2O_5$, as well as mixed oxides such as $Ni_2V_2O_7$ and $Ni_3V_2O_8$ can be used. One skilled in the art would appreciate that a number of other related metal and metal oxide catalysts, and their combinations, can also be used. Any reactors for the conversion reactions can be used such as for example continuous flow reactors under the appropriate reaction conditions at suitable temperatures and pressures.

The significant advantage of the disclosed new processing of heavy oils into methanol is that the heavy oils are not processed (refined) in the usual way but that substantially all of them (i.e., at least 90%) are converted to give close to a 2:1 molar ratio of hydrogen and carbon monoxide, a ratio which is ideally suited for the subsequent production of methanol. A further advantage of the invention is that carbon dioxide is not released into the atmosphere or sequestered but is recycled via its conversion to methanol, dimethyl ether, as well as to their derived products. This provides for significant economical and environmental advantages.

The "heaviness" of heavy oil is primarily due to the relatively high proportion of complex, high molecular weight, non-paraffinic compounds and a relatively low proportion of volatile, low molecular weight compounds. The pretreatment renders the heavy oil free-flowing similar to regular fuel oil by reducing its viscosity and providing a good API index. For example, the API of Venezuela's Orinoco extra-heavy crude oil generally lies in the range 8-15, while Canadian extra-heavy crude can be in the range of 8-11. The present processes increase the API index of the oil to 30 to 40 and then converts the treated oil to methanol.

In a further embodiment of the invention, the heavy oil sources, such as tar sands, can be in situ gasified using any available energy source including combustion of a hydrocarbon source or atomic energy to produce steam and to produce a 2:1 mixture of carbon monoxide and hydrogen needed for the methanol synthesis. Carbon dioxide formed in the process is captured and recycled in the bi-reforming treatment, thus not released in to the atmosphere. If desired, methanol produced in the disclosed processes is converted to dimethyl ether via its dehydration. Dehydration can be achieved over a suitable dry silica catalyst or a polymeric perfluoroalkanesulfonic acid catalyst at a temperature of from about 100° C. to 200° C. An example of such catalyst is Nafion-H.

This embodiment of the invention can be illustrated by the following:

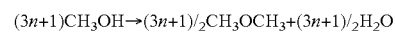

$(3n+1)CH_3OH \rightarrow (3n+1)/_2CH_3OCH_3+(3n+1)/_2H_2O$

In a further embodiment, the production of dimethyl ether can also be carried out by the recycling of water formed in the dehydration step into reaction step C.

In this embodiment, the water formed during the dehydration of methanol can be completely reused.

The advantage of the present invention is that it allows for the efficient conversion of heavy oils bypassing their conventional difficult and environmentally harmful processing to produce methanol and/or dimethyl ether with the substantial utilization of carbon dioxide formed to produce methanol or dimethyl ether. This represents an efficient and economical new way of methanol or dimethyl ether production from heavy oils, as well as an efficient recycling of carbon dioxide. The process is also characterized by significantly decreased coke and carbon residue formation, as presence of steam in the bi-reforming process retards such processes.

The processing of the invention also allows for recycling of the water produced from the dehydration of methanol to dimethyl ether, thus decreasing the need of external water, which is significant to avoid water resource depletion.

As can be appreciated by one of skilled in the art, the energy required in the processes of the invention can come from any suitable energy source, including, but not limited to burning part of the heavy oil sources or use of any alternative energy sources including solar, wind etc., or atomic energy.

In summary, the processes of the invention allow the efficient and environmentally friendly and economic processing of heavy oils to methanol and dimethyl ether, as well as their derived products.

EXAMPLES

The following examples illustrate the preferred embodiments of the invention without limiting them.

Example 1

Utilization of any heavy crude oils recovered from varied sources, such as tar sands, shale oils, heavy residues via thermal or catalytic break down of their extremely heavy asphaltenes or maltenes residues with simultaneous removal of sulfur and metal impurities for their conversion to methanol or dimethyl ether by passing conventional refining using the bi-reforming process for reacting heavy hydrocarbon oils with water and carbon dioxide.

Example 2

Purified heavy crude oils produced from any source are subjected to the bi-reforming process in a flow reactor over a catalyst such as NiO at a temperature of about 800° C. to 1100° C. preferentially between 800-850° C. Catalysts include varied metal and metal oxides such as V, Ti, Ga, Mg, Cu, Ni, Mo, Bi, Fe, Mn, Co, Nb, Zr, or Sn used as single metal, metal oxides or their combination. They can be supported on suitable support, preferentially suitably large nanostructured surface such as fumed silica or aluminum. A preferred catalyst is NiO on fused alumina support. The processing provides a mixture of CO and $H_2$.

Example 3

Adjusting the mixture obtained in Example 2 to give CO and $H_2$ composition of 2:1 mole ratio suitable for the production of methanol.

Example 4

Hydrogen and carbon monoxide produced in approximately 2:1 ratio are converted to produce methanol under catalytic reaction conditions using usual copper and related catalysts.

Example 5

The methanol produced in Example 4 is dehydrated to dimethyl ether using a solid acid catalyst such as Nafion H between 100° C. to 200° C.

Example 6

The water formed during dehydration of methanol to dimethyl ether is recycled in the bi-reforming of heavy hydrocarbon oils.

The invention described and claimed herein is not to be limited in scope by the specific embodiments herein disclosed, as these embodiments are intended as illustrative of several aspects of the invention. Any equivalent embodiments are intended to be within the scope of this invention, as they will become apparent to those skilled in the art from the present description. Such embodiments are also intended to fall within the scope of the appended claims.

What is claimed is:

1. A method for producing methanol, which comprises:
increasing the API index of heavy oils by breaking down asphaltene and maltene components to reduce viscosity, remove harmful impurities and form treated heavy oils having an API index of between 30 and 40;
reacting the treated heavy oils with water under steam reforming reaction conditions sufficient to form a mixture of hydrogen and carbon monoxide;
reacting the treated heavy oils and carbon dioxide under dry reforming reaction conditions sufficient to form a mixture of hydrogen and carbon monoxide;
combining the hydrogen and carbon monoxide mixtures produced in the steam and dry reforming steps to form a mixture of hydrogen and carbon monoxide at a molar ratio of between about 2:1 and 2.1:1; and
reacting the mixture of hydrogen and carbon monoxide without separation of its components under conditions sufficient to exclusively form methanol;
wherein the heavy oils are not gasified in the presence of oxygen.

2. The method of claim 1 wherein the heavy oils are obtained from any suitable source including tar sands, oil shales, various heavy oil deposits or residues thereof and are treated to be rendered less viscous and to remove sulfur and metals.

3. The method of claim 2, wherein the heavy oils are treated to remove at least 99.8% of sulfur and metals.

4. The method of claim 1, wherein the molar ratio of hydrogen to carbon monoxide produced is at approximately 2.05:1.

5. The method of claim 1, wherein the steam reforming and dry reforming steps are conducted together in a single step at an appropriate temperature and in an appropriate molar ratio to form the methanol.

6. A method for producing methanol, which comprises:
increasing the API index of heavy oils by breaking down asphaltene and maltene components to reduce viscosity, remove harmful impurities and form treated heavy oils having an API index of between 30 and 40;
reacting the treated heavy oils with water under steam reforming reaction conditions sufficient to form a mixture of hydrogen and carbon monoxide;
reacting the treated heavy oils and carbon dioxide under dry reforming reaction conditions sufficient to form a mixture of hydrogen and carbon monoxide, wherein the steam reforming and dry reforming steps are conducted together in a single step over a catalyst at a temperature of from about 800° C. to 1100° C.;
combining the hydrogen and carbon monoxide mixtures produced in the steam and dry reforming steps to form a mixture of hydrogen and carbon monoxide at a molar ratio of between about 2:1 and 2.1:1; and
reacting the mixture of hydrogen and carbon monoxide without separation of its components under conditions sufficient to exclusively form methanol;
wherein the heavy oils are not gasified in the presence of oxygen.

7. The method of claim 6, wherein the catalyst includes a single metal catalyst, a single metal oxide catalyst, a mixed catalyst of a metal and a metal oxide or a mixed catalyst of at least one metal oxide and another metal oxide, with the catalyst optionally provided upon an oxide support.

8. The method of claim 7, wherein the catalyst is supported on a high surface area or nanostructured fumed alumina or fumed silica.

9. The method of claim 8, wherein the catalyst includes V, Ti, Ga, Mg, Cu, Ni, Mo, Bi, Fe, Mn, Co, Nb, Zr, La or Sn or an oxide thereof.

10. The method of claim 9, wherein the catalyst is NiO or a mixed catalyst of NiO, $V_2O_5:Ni_2O_3$, $Ni_2V_2O_7$ and $Ni_3V_2O_5$.

11. The method of claim 10, wherein the catalyst is NiO supported on fumed alumina or $NiO/V_2O_5$ supported on fumed silica.

* * * * *